(12) United States Patent
Wojcik et al.

(10) Patent No.: US 10,959,690 B2
(45) Date of Patent: Mar. 30, 2021

(54) OVERLAPPING STEPPED STANDARD DR DETECTOR FOR LONG LENGTH IMAGING

(71) Applicant: CARESTREAM HEALTH, INC., Rochester, NY (US)

(72) Inventors: Timothy J. Wojcik, Rochester, NY (US); Scott T. MacLaughlin, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 45 days.

(21) Appl. No.: 16/659,632

(22) Filed: Oct. 22, 2019

(65) Prior Publication Data

US 2020/0121270 A1 Apr. 23, 2020

Related U.S. Application Data

(60) Provisional application No. 62/748,565, filed on Oct. 22, 2018.

(51) Int. Cl.
*A61B 6/00* (2006.01)

(52) U.S. Cl.
CPC .......... *A61B 6/4266* (2013.01); *A61B 6/4233* (2013.01)

(58) Field of Classification Search
CPC ..... A61B 6/4233; A61B 6/4283; A61B 6/405; A61B 6/56; A61B 6/4405; A61B 6/4266; G01T 1/16; G01T 1/2018; G01T 1/2012; G01T 1/2006; G01T 1/20; G01T 1/24
See application file for complete search history.

(56) References Cited

U.S. PATENT DOCUMENTS 9,820,703 B2 * 11/2017 Wojcik ................ A61B 6/4283

* cited by examiner

*Primary Examiner* — Don K Wong

(57) ABSTRACT

A long length radiographic imaging system uses a plurality of overlapped radiographic detectors each comprising a housing having stepped housing edges at opposite sides of each detector. The stepped housing edges mate with each other to easily form overlapped aligned detectors for simultaneously capturing a long length radiographic image of a subject in a single exposure of the x-ray source.

6 Claims, 8 Drawing Sheets

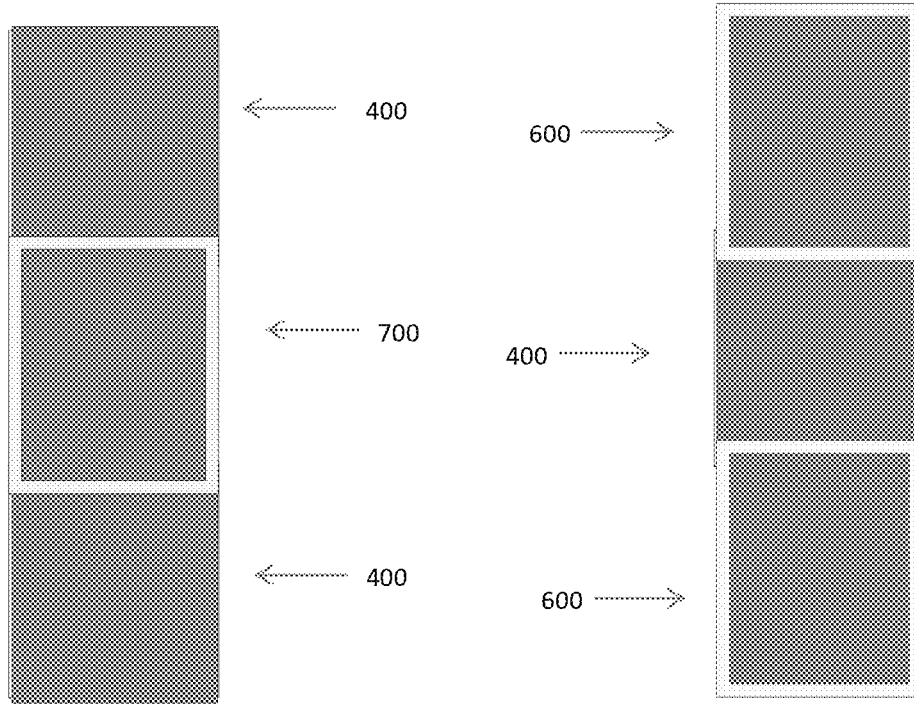
FIG. 10  FIG. 11
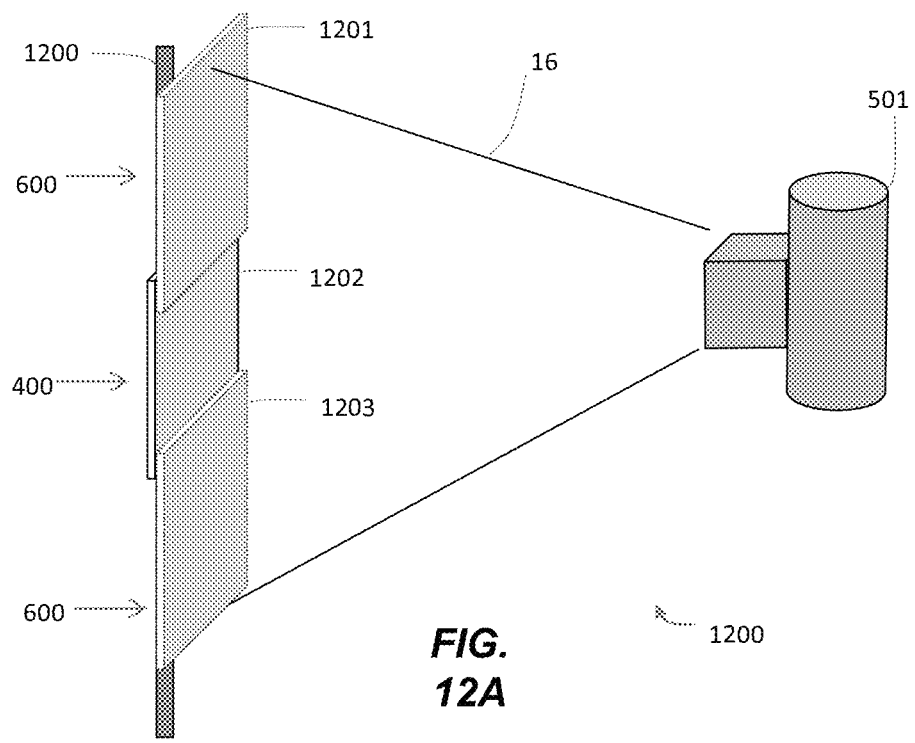
FIG. 12A

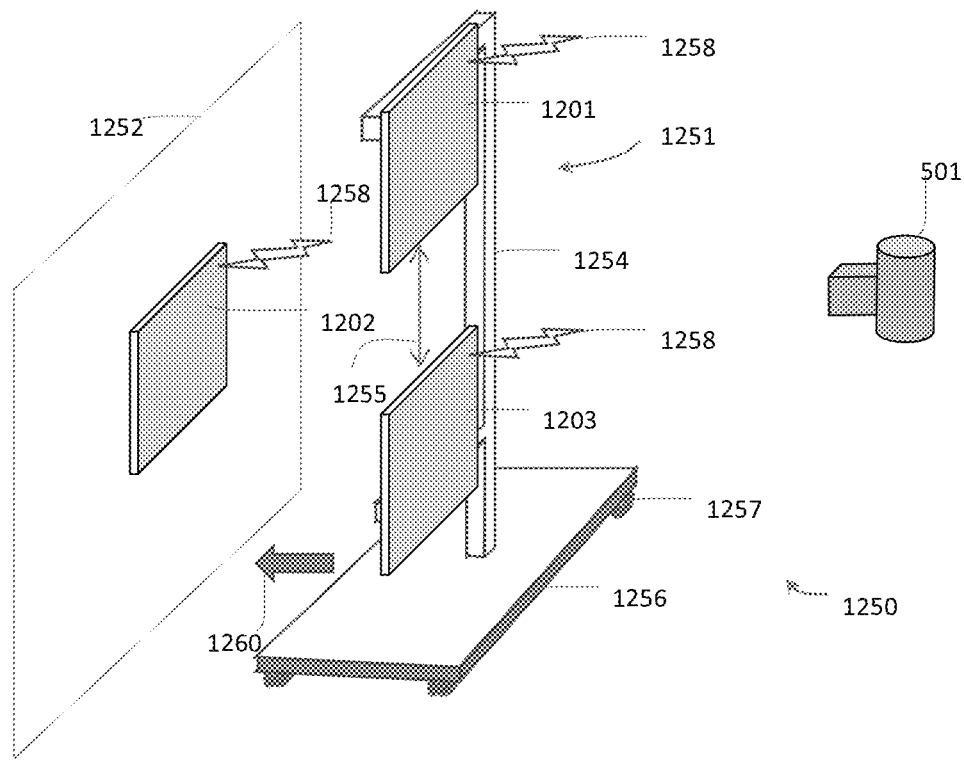
FIG.
12B
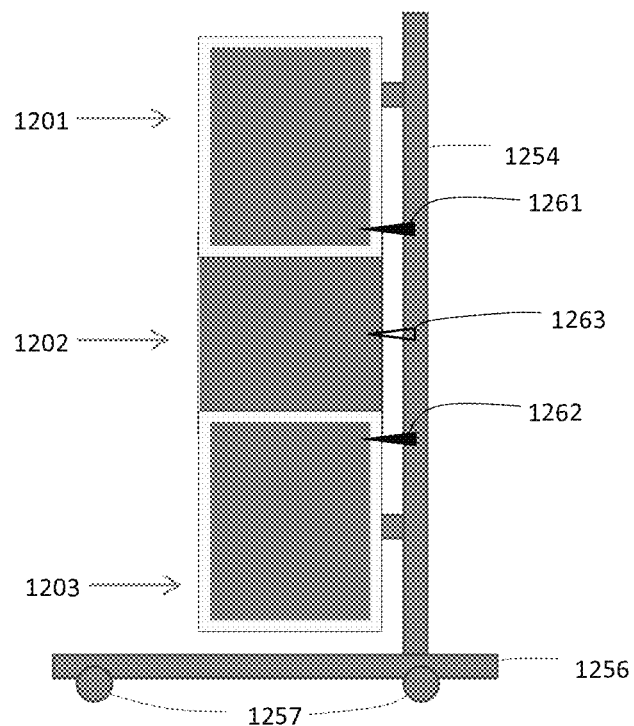
FIG.
12C

OVERLAPPING STEPPED STANDARD DR DETECTOR FOR LONG LENGTH IMAGING

CROSS REFERENCE TO RELATED APPLICATIONS

This application claims priority to U.S. Patent Application Ser. No. 62/748,565, filed Oct. 22, 2018, in the name of Wojcik et al., and entitled OVERLAPPING STEPPED STANDARD DR DETECTOR FOR LONG LENGTH IMAGING.

BACKGROUND OF THE INVENTION

The subject matter disclosed herein relates to digital radiography (DR) imaging, in particular, to long-length imaging that requires multiple DR detectors.

Special cassettes and films of extended length are sometimes used when imaging a long segment of a subject, such as a human body, with an analog screen-film technique. An x-ray source and the cassette are both centered to the subject to be examined and an x-ray collimator is adjusted to cover the imaging area, whereby a single x-ray exposure is performed. For long-length imaging applications this would require separate exposures to be taken at different regions of the subject. In order to create a large, single composite image for diagnosis, the individually captured images of the subject need to be stitched together using digital computer-implemented reconstruction techniques.

Two primary approaches are available to acquire long-length imaging exams with flat-panel detectors. In both methods, the detector moves from one imaging position to the next behind the subject. In one known embodiment, the x-ray energy source moves (rotates or tilts) in order to track and expose the detector. In this x-ray source tilting method, the central x-ray pointing direction varies from one exposure position to the next to deliver the x-rays to the detector. In another known embodiment, the x-ray source focal spot position is not stationary, but translates synchronously with the DR detector parallel to the detector's axis of travel.

There are advantages to both embodiments. For example, the tilt method is free of parallax artifacts inherent in the x-ray source translation method. Because of parallax distortion, the geometric integrity of the subject's features in the stitched image may be degraded, particularly in the stitch overlap regions. A high-precision hardware encoder reports the exact detector travel distance between exposures. In a direction transverse to the detector motion axis, software automatically analyzes the subject's features in the overlap regions to find the best alignment between any two adjacent images. The total stitch error has been demonstrated to be small under stringent exposure conditions.

Automatic exposure control can be used during the long-length imaging exams in order to apply just the right amount of exposure to each region of the subject for image quality. Software may also automatically adjust exposure discrepancies and compensate for the latitude differences, therefore providing optimized image presentation for each image. The image-processing reconstruction algorithm stitches together the individually optimized, display-presentation-ready images to create a smooth and seamless composite single image for diagnosis. The seam line between any two images may be blended without any visible artifacts during this digital process. Such imaging software should be able to adjust and fine-tune stitch positions to compensate for movement of the subject during the exam to avoid exposure retakes. In all of the examples just described, it would be advantageous if multiple DR detectors could be used to simultaneously capture a composite radiographic image of a subject in a single exposure.

The discussion above is merely provided for general background information and is not intended to be used as an aid in determining the scope of the claimed subject matter.

BRIEF DESCRIPTION OF THE INVENTION

A long length radiographic imaging system uses a plurality of overlapped radiographic detectors each comprising a housing having stepped housing edges at opposite sides thereof. The stepped housing edges mate with each other to easily form overlapped aligned detectors for simultaneously capturing a long length radiographic image of a subject in a single exposure of the x-ray source.

In one embodiment, a long length radiographic imaging system has a processing system, an x-ray source communicatively coupled to the processing system, and a plurality of overlapping radiographic detectors communicatively coupled to the processing system. The plurality of overlapping radiographic detectors each have a housing with stepped housing edges at opposite sides of each detector. The stepped housing edges are configured to mate with a stepped housing edge of an adjacent overlapped radiographic detector. The plurality of overlapping radiographic detectors are configured to simultaneously capture a radiographic image of a portion of a subject in a single exposure.

In one embodiment, a digital radiographic detector includes a housing and an imaging array, wherein the housing has stepped edges at opposite edges thereof. One of the stepped housing edges faces upward and a second one of the stepped housing edges faces downward. The stepped edges are configured to mate with a stepped housing edge of another adjacent similarly constructed digital radiographic detector.

In one embodiment, a long length radiographic imaging assembly includes a plurality of overlapping radiographic detectors each with a housing having stepped edges at opposite sides. The stepped housing edges are configured to mate with a stepped edge of an adjacent overlapped radiographic detector. The plurality of radiographic detectors are configured to simultaneously capture a radiographic image of a portion of a subject in response to a single x-ray exposure.

The summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications. The drawings below are intended to be drawn neither to any precise scale with respect to relative size, angular relationship, relative position, or timing relationship, nor to any combinational relationship with respect to interchangeability, substitution, or representation of a required implementation.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description.

This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 10 is a top view of an exemplary arrangement of multiple DR detectors in a radiographic imaging system according to the embodiment of FIG. 8;

FIG. 11 is a top view of an exemplary arrangement of multiple DR detectors in a radiographic imaging system according to the embodiment of FIG. 9;

FIG. 12A is a perspective view of an exemplary imaging system implementing an arrangement of DR detectors according to one embodiment;

FIG. 12B is a perspective view of an exemplary imaging system implementing an arrangement of DR detectors according to one embodiment;

FIG. 12C is a front view of the exemplary transport apparatus of FIG. 12B;

DETAILED DESCRIPTION OF THE INVENTION

Figure 1:
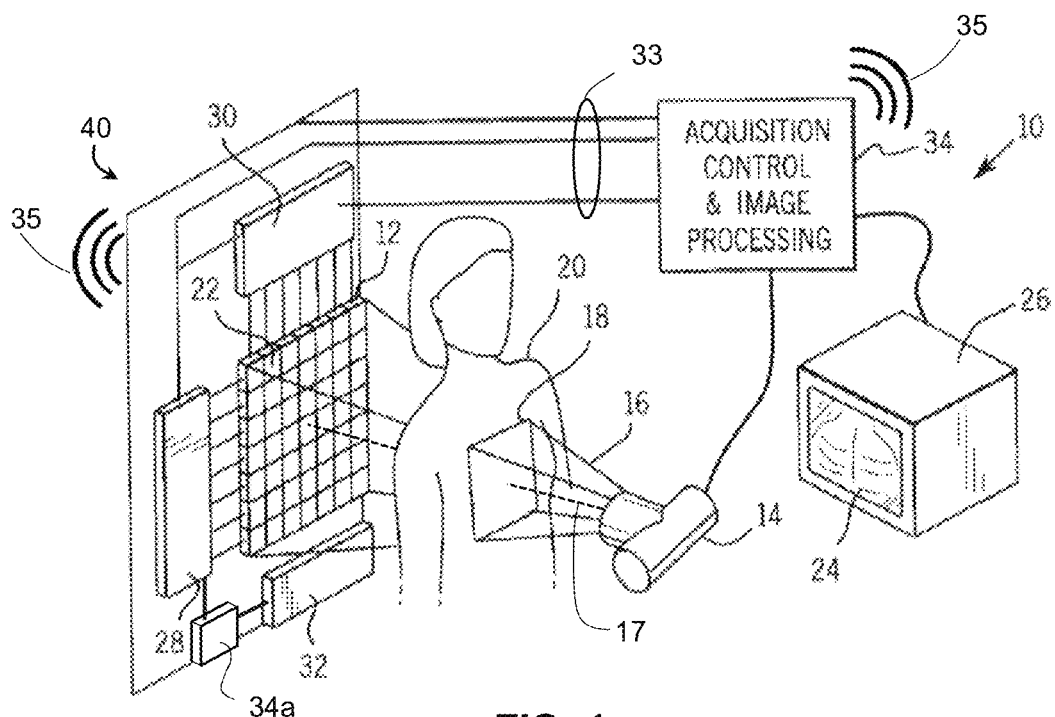
FIG. 1 is a diagram of an exemplary radiographic imaging system.

FIG. 1 is a perspective view of a digital radiographic (DR) imaging system 10 that may include a generally curved or planar DR detector 40 (shown in a planar embodiment and without a housing for clarity of description), an x-ray source 14 configured to generate radiographic energy (x-ray radiation), and a digital monitor, or electronic display, 26 configured to display images captured by the DR detector 40, according to one embodiment. The DR detector 40 may include a two dimensional array 12 of detector cells 22 (photosensors), arranged in electronically addressable rows and columns. The DR detector 40 may be positioned to receive x-rays 16 passing through a subject 20 during a radiographic energy exposure, or radiographic energy pulse, emitted by the x-ray source 14. As shown in FIG. 1, the radiographic imaging system 10 may use an x-ray source 14 that emits collimated x-rays 16, e.g. an x-ray beam, selectively aimed at and passing through a preselected region 18 of the subject 20. The x-ray beam 16 may be attenuated by varying degrees along its plurality of rays according to the internal structure of the subject 20, which attenuated rays are detected by the array 12 of photosensitive detector cells 22. The curved or planar DR detector 40 is positioned, as much as possible, in a perpendicular relation to a substantially central ray 17 of the plurality of rays 16 emitted by the x-ray source 14. In a curved array embodiment, the source 14 may be centrally positioned such that a larger percentage, or all, of the photosensitive detector cells are positioned perpendicular to incoming x-rays from the centrally positioned source 14. The array 12 of individual photosensitive cells (pixels) 22 may be electronically addressed (scanned) by their position according to column and row. As used herein, the terms "column" and "row" refer to the vertical and horizontal arrangement of the photo sensor cells 22 and, for clarity of description, it will be assumed that the rows extend horizontally and the columns extend vertically. However, the orientation of the columns and rows is arbitrary and does not limit the scope of any embodiments disclosed herein. Furthermore, the term "subject" may be illustrated as a human patient in the description of FIG. 1, however, a subject of a DR imaging system, as the term is used herein, may be a human, an animal, an inanimate object, or a portion thereof.

In one exemplary embodiment, the rows of photosensitive cells 22 may be scanned one or more at a time by electronic scanning circuit 28 so that the exposure data from the array 12 may be transmitted to electronic read-out circuit 30. Each photosensitive cell 22 may independently store a charge proportional to an intensity, or energy level, of the attenuated radiographic radiation, or x-rays, received and absorbed in the cell. Thus, each photosensitive cell, when read-out, provides information defining a pixel of a radiographic image 24, e.g. a brightness level or an amount of energy absorbed by the pixel, that may be digitally decoded by image processing electronics 34 and transmitted to be displayed by the digital monitor 26 for viewing by a user. An electronic bias circuit 32 is electrically connected to the two-dimensional detector array 12 to provide a bias voltage to each of the photosensitive cells 22.

Each of the bias circuit 32, the scanning circuit 28, and the read-out circuit 30, may communicate with an acquisition control and image processing unit 34 over a connected cable 33 (wired), or the DR detector 40 and the acquisition control and image processing unit 34 may be equipped with a wireless transmitter and receiver to transmit radiographic image data wirelessly 35 to the acquisition control and image processing unit 34. The acquisition control and image processing unit 34 may include a processor and electronic memory (not shown) to control operations of the DR detector 40 as described herein, including control of circuits 28, 30, and 32, for example, by use of programmed instructions, and to store and process image data. The acquisition control and image processing unit 34 may also be used to control activation of the x-ray source 14 during a radiographic exposure, controlling an x-ray tube electric current magnitude, and thus the fluence of x-rays in x-ray beam 16, and/or the x-ray tube voltage, and thus the energy level of the x-rays in x-ray beam 16. The acquisition control and image processing unit 34 may be referred to herein as a host system or a central processing system. Typically, such a host system may be configured to control and manage operations of the radiographic imaging system 10 automatically or by providing an operator with various input devices to control exposure operations.

A portion or all of the acquisition control and image processing unit 34 functions may reside in the detector 40 in an on-board processing system 34a which may include a processor and electronic memory to control operations of the DR detector 40 as described herein, including control of circuits 28, 30, and 32, by use of programmed instructions, and to store and process image data similar to the functions of standalone acquisition control and image processing system 34. The on-board processing system 34a may include sufficient electronic memory to store several raw and/or fully processed (e.g., gain, offset, and defect corrected) DR images. The image processing system may perform image acquisition and image disposition functions as described herein. The image processing system 34a may control image transmission and image processing and image correction on board the detector 40 based on instructions or other commands transmitted from the acquisition control and image processing unit 34, and transmit corrected digital image data therefrom. Alternatively, acquisition control and image processing unit 34 may receive raw image data from the detector 40 and process the image data and store it, or it may store raw unprocessed image data in local memory, or in remotely accessible memory.

With regard to a direct detection embodiment of DR detector 40, the photosensitive cells 22 may each include a sensing element sensitive to x-rays, i.e. it absorbs x-rays and generates an amount of charge carriers in proportion to a magnitude of the absorbed x-ray energy. A switching element may be configured to be selectively activated to read out the charge level of a corresponding x-ray sensing element. With regard to an indirect detection embodiment of DR detector 40, photosensitive cells 22 may each include a sensing element sensitive to light rays in the visible spectrum, i.e. it absorbs light rays and generates an amount of charge carriers in proportion to a magnitude of the absorbed light energy, and a switching element that is selectively activated to read the charge level of the corresponding sensing element. A scintillator, or wavelength converter, may be disposed over the light sensitive sensing elements to convert incident x-ray radiographic energy to visible light energy. Thus, in the embodiments disclosed herein, it should be noted that the DR detector 40 (or DR detector 300 in FIG. 3 or DR detector 400 in FIG. 4) may include an indirect or direct type of DR detector.

Examples of sensing elements used in sensing array 12 include various types of photoelectric conversion devices (e.g., photosensors) such as photodiodes (P-N or PIN diodes), photo-capacitors (MIS), photo-transistors or photoconductors. Examples of switching elements used for signal read-out include a-Si TFTs, oxide TFTs, MOS transistors, bipolar transistors and other p-n junction components.

Figure 2:
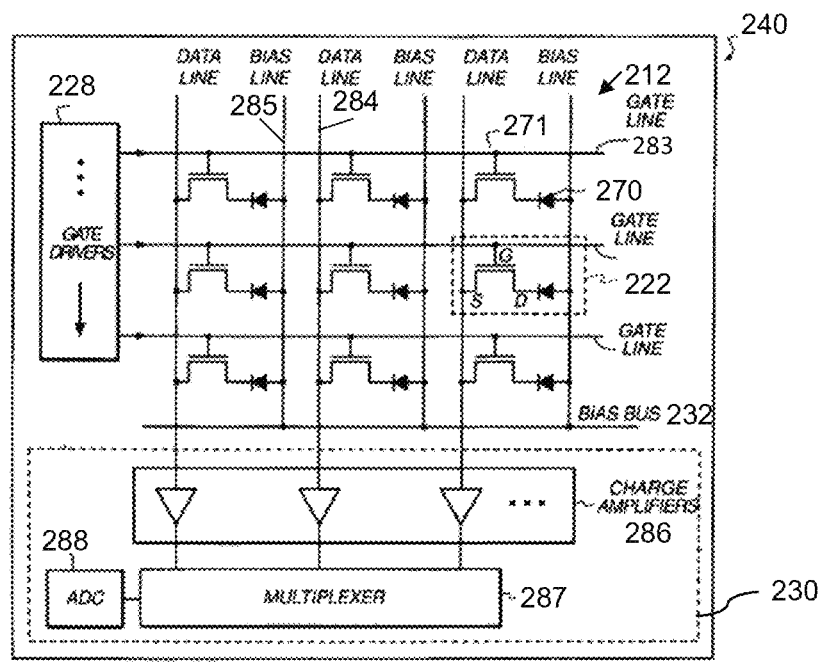
FIG. 2 is a schematic diagram of an exemplary imaging array for a radiographic detector.

FIG. 2 is a schematic diagram 240 of a portion of a two-dimensional array 12 for a DR detector 40. The array of photosensor cells 212, whose operation may be consistent with the photosensor array 12 described above, may include a number of hydrogenated amorphous silicon (a-Si:H) n-i-p photodiodes 270 and thin film transistors (TFTs) 271 formed as field effect transistors (FETs) each having gate (G), source (S), and drain (D) terminals. In embodiments of DR detector 40 disclosed herein, such as a multilayer DR detector (400 of FIG. 4), the two-dimensional array of photosensor cells 12 may be formed in a device layer that abuts adjacent layers of the DR detector structure, which adjacent layers may include a rigid glass layer or a flexible polyimide layer or a layer comprising carbon fiber without any adjacent rigid layers. A plurality of gate driver circuits 228 may be electrically connected to a plurality of gate lines 283 which control a voltage applied to the gates of TFTs 271, a plurality of readout circuits 230 may be electrically connected to data lines 284, and a plurality of bias lines 285 may be electrically connected to a bias line bus or a variable bias reference voltage line 232 which controls a voltage applied to the photodiodes 270. Charge amplifiers 286 may be electrically connected to the data lines 284 to receive signals therefrom. Outputs from the charge amplifiers 286 may be electrically connected to a multiplexer 287, such as an analog multiplexer, then to an analog-to-digital converter (ADC) 288, or they may be directly connected to the ADC, to stream out the digital radiographic image data at desired rates. In one embodiment, the schematic diagram of FIG. 2 may represent a portion of a DR detector 40 such as an a-Si:H based indirect flat panel, curved panel, or flexible panel imager.

Incident x-rays, or x-ray photons, 16 are converted to optical photons, or light rays, by a scintillator, which light rays are subsequently converted to electron-hole pairs, or charges, upon impacting the a-Si:H n-i-p photodiodes 270. In one embodiment, an exemplary detector cell 222, which may be equivalently referred to herein as a pixel, may include a photodiode 270 having its anode electrically connected to a bias line 285 and its cathode electrically connected to the drain (D) of TFT 271. The bias reference voltage line 232 can control a bias voltage of the photodiodes 270 at each of the detector cells 222. The charge capacity of each of the photodiodes 270 is a function of its bias voltage and its capacitance. In general, a reverse bias voltage, e.g. a negative voltage, may be applied to the bias lines 285 to create an electric field (and hence a depletion region) across the pn junction of each of the photodiodes 270 to enhance its collection efficiency for the charges generated by incident light rays. The image signal represented by the array of photosensor cells 212 may be integrated by the photodiodes while their associated TFTs 271 are held in a non-conducting (off) state, for example, by maintaining the gate lines 283 at a negative voltage via the gate driver circuits 228. The photosensor cell array 212 may be read out by sequentially switching rows of the TFTs 271 to a conducting (on) state by means of the gate driver circuits 228. When a row of the pixels 22 is switched to a conducting state, for example by applying a positive voltage to the corresponding gate line 283, collected charge from the photodiode in those pixels may be transferred along data lines 284 and integrated by the external charge amplifier circuits 286. The row may then be switched back to a non-conducting state, and the process is repeated for each row until the entire array of photosensor cells 212 has been read out. The integrated signal outputs are transferred from the external charge amplifiers 286 to an analog-to-digital converter (ADC) 288 using a parallel-to-serial converter, such as multiplexer 287, which together comprise read-out circuit 230.

This digital image information may be subsequently processed by image processing system 34 to yield a digital image which may then be digitally stored and immediately displayed on monitor 26, or it may be displayed at a later time by accessing the digital electronic memory containing the stored image. The flat panel DR detector 40 having an imaging array as described with reference to FIG. 2 is capable of both single-shot (e.g., static, radiographic) and continuous (e.g., fluoroscopic) image acquisition.

Figure 3:
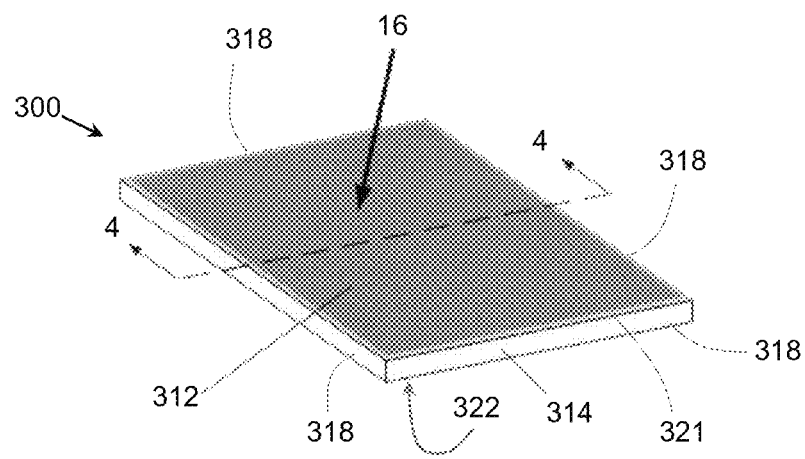
FIG. 3 shows a perspective view of an exemplary portable wireless DR detector.

FIG. 3 shows a perspective view of an exemplary prior art generally rectangular, planar, portable wireless DR detector 300 according to an embodiment of DR detector 40 disclosed herein. The DR detector 300 may include a flexible substrate to allow the DR detector to capture radiographic images in a curved orientation. The flexible substrate may be fabricated in a permanent curved orientation, or it may remain flexible throughout its life to provide an adjustable curvature in two or three dimensions, as desired. The DR detector 300 may include a similarly flexible housing portion 314 that surrounds a multilayer structure comprising a flexible photosensor array portion 22 of the DR detector 300. The housing portion 314 of the DR detector 300 may include a continuous, rigid or flexible, x-ray opaque material or, as used synonymously herein a radio-opaque material, surrounding an interior volume of the DR detector 300. The housing portion 314 may include four flexible edges 318, extending between the top side 321 and the bottom side 322, and arranged substantially orthogonally in relation to the top and bottom sides 321, 322. The bottom side 322 may be continuous with the four edges and disposed opposite the top side 321 of the DR detector 300. The top side 321 comprises a top cover 312 attached to the housing portion 314 which, together with the housing portion 314, substantially encloses the multilayer structure in the interior volume of the DR detector 300. The top cover 312 may be attached to the housing 314 to form a seal therebetween, and be made of a material that passes x-rays 16 without significant attenuation thereof, i.e., an x-ray transmissive material or, as used synonymously herein, a radiolucent material, such as a carbon fiber plastic, polymeric, or other plastic based material.

Figure 4:
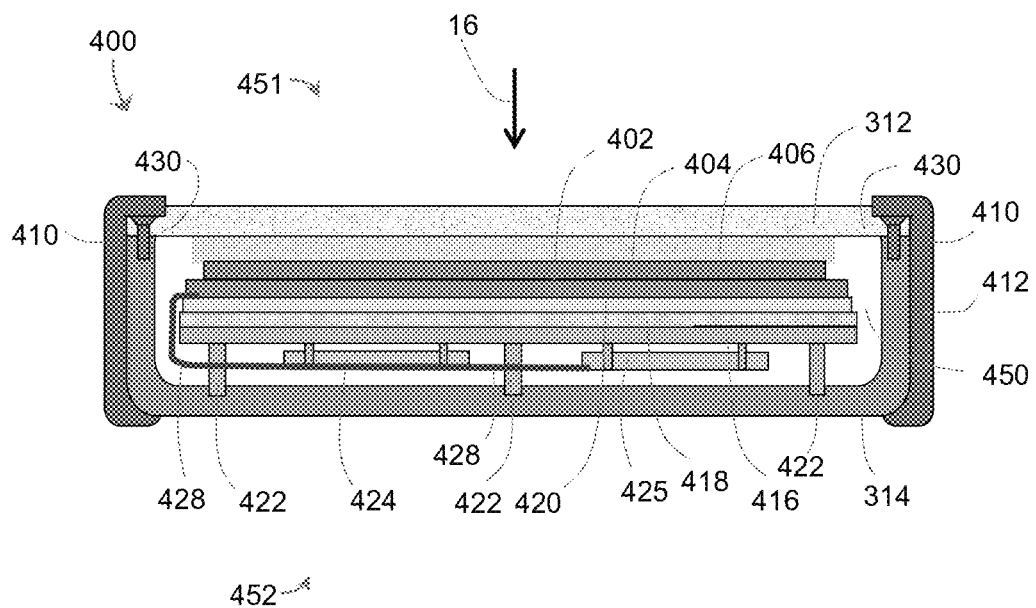
FIG. 4 is a cross-section of a portion of the exemplary portable wireless DR detector of FIG. 3 along section line 4-4.

With reference to FIG. 4, there is illustrated in schematic form an exemplary cross-section view along section 4-4 of the exemplary embodiment of the DR detector 300 (FIG. 3). For spatial reference purposes, one major surface of the DR detector 400 may be referred to as the top side 451 and a second major surface may be referred to as the bottom side 452, as used herein. The multilayer structure may be disposed within the interior volume 450 enclosed by the housing 314 and top cover 312 and may include a flexible curved or planar scintillator layer 404 over a curved or planar the two-dimensional imaging sensor array 12 shown schematically as the device layer 402. The scintillator layer 404 may be directly under (e.g., directly connected to) the substantially planar top cover 312, and the imaging array 402 may be directly under the scintillator 404. Alternatively, a flexible layer 406 may be positioned between the scintillator layer 404 and the top cover 312 as part of the multilayer structure to allow adjustable curvature of the multilayer structure and/or to provide shock absorption. The flexible layer 406 may be selected to provide an amount of flexible support for both the top cover 312 and the scintillator 404, and may comprise a foam rubber type of material. The layers just described comprising the multilayer structure each may generally be formed in a rectangular shape and defined by edges arranged orthogonally and disposed in parallel with an interior side of the edges 318 of the housing 314, as described in reference to FIG. 3.

Figure 6:
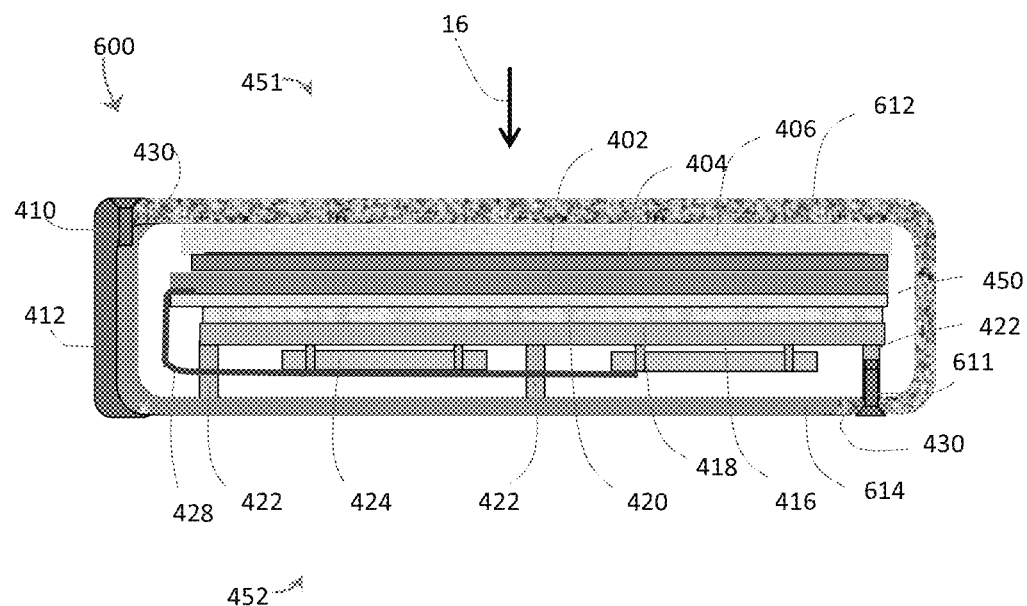
FIG. 6 is a cross-section of a portion of an exemplary portable wireless DR detector according to one embodiment.

A substrate layer 420 may be disposed under the imaging array 402, such as a rigid glass layer, in one embodiment, or a flexible substrate comprising polyimide or carbon fiber upon which the array of photosensors 402 may be formed to allow adjustable curvature of the array, and may comprise another layer of the multilayer structure. Under the substrate layer 420 a flexible or rigid radio-opaque shield layer 418 may be used as an x-ray blocking layer to help prevent scattering of x-rays passing through the substrate layer 420 as well as to block x-rays reflected from other surfaces in the interior volume 450. The flexible or rigid radio-opaque shield layer 418 may be attached to the layers above it, as shown in FIG. 4 or 6, or separated therefrom as part of the frame support and electronics portion of the interior layers. Readout electronics, including the scanning circuit 28, the read-out circuit 30, the bias circuit 32, and processing system 34a (all of FIG. 1) may be formed adjacent the imaging array 402 or, as shown, may be disposed below a flexible or rigid frame support member 416 in the form of integrated circuits (ICs) electrically connected to printed circuit boards 424, 425. The flexible or rigid frame support member 416 may be attached to the layers above it, as shown in FIG. 4 or 6, or separated therefrom as part of a separate frame support and electronics portion of the interior layers. The imaging array 402 may be electrically connected to the readout electronics 424 (ICs) over a flexible connector 428 which may comprise a plurality of flexible, sealed conductors known as chip-on-film (COF) connectors.

X-ray flux may pass through the radiolucent top panel cover 312, in the direction represented by an exemplary x-ray beam 16, and impinge upon scintillator 404 where stimulation by the high-energy x-rays 16, or photons, causes the scintillator 404 to emit lower energy photons as visible light rays which are then received in the photosensors of imaging array 402. The frame support member 416 may connect the multilayer structure to the housing 314 and may further operate as a shock absorber by disposing elastic pads (not shown) between the frame support beams 422 and the housing 314. Fasteners 410 may be used to attach the top cover 312 to the housing 314 and create a seal therebetween in the region 430 where they come into contact. In one embodiment, an external bumper 412 may be attached along the edges 318 of the DR detector 400 to provide additional shock-absorption.

Figure 5:
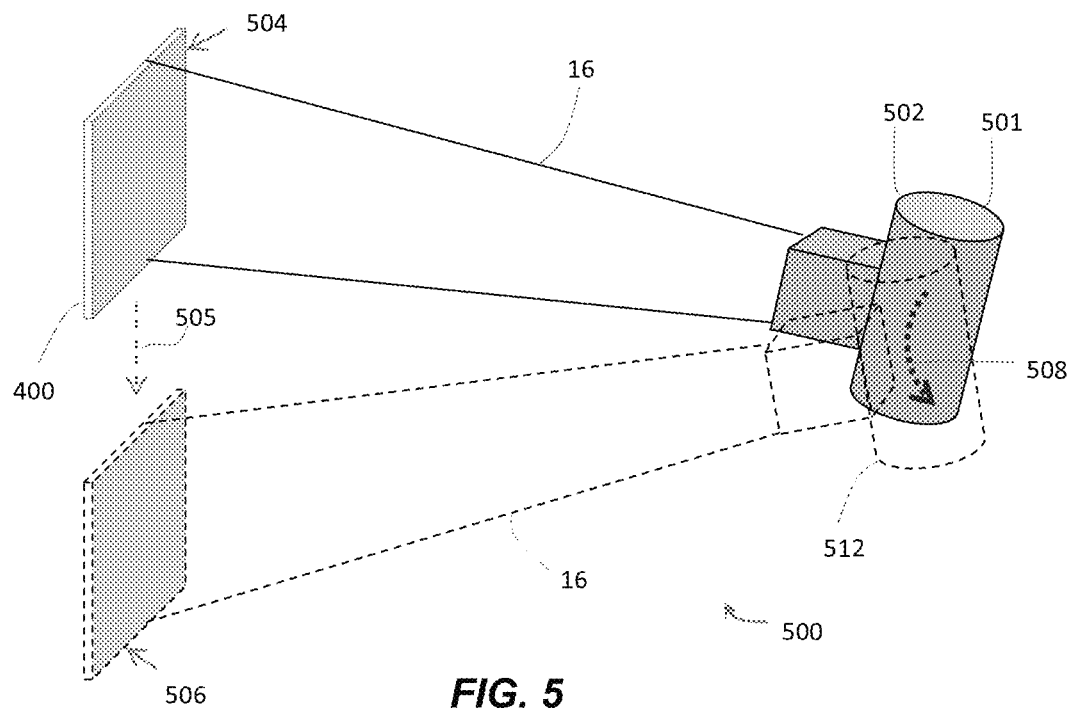
FIG. 5 is a diagram of an exemplary radiographic imaging system illustrating positioning of the radiographic energy source and the DR detector.

FIG. 5 illustrates operation of an embodiment of an imaging system 500 which may be used for long-length radiographic imaging of a stationary subject (not shown) positioned between an x-ray source 501 and DR detector 400. The x-ray radiation source 501 in the first position 502 is aimed at DR detector 400 in position 504 to capture a first radiographic image of the subject. In the embodiment shown in FIG. 5, the x-ray radiation source may be tilted in the direction indicated by arrow 508 to a second position 512 and aimed at DR detector 400 in position 506 to capture a second image of the stationary subject, wherein the first and second images each include an image of a different region of the same subject. In the embodiment of FIG. 5, a single DR detector 400 may be moved in the direction indicated by arrow 505 from the first position 504 to the second position 506 to capture the two images of the subject as just described. In another embodiment, two or more separate DR detectors 400 may be used, one in each of positions 504 and 506, and in positions in between, wherein each DR detector 400 is exposed to one radiographic pulse from the x-ray source 501 firing energy pulses at positions 502 and 512, and in corresponding positions in between. In another embodiment, the DR detector 400 may be moved to one or more intermediate positions between positions 504 and 506, with corresponding intermediate tilt positions of the x-ray source 501 between positions 502 and 512 to capture one or more additional radiographic images. In another embodiment, the x-ray source may be attached to a support at a fixed angle such that the x-ray source 501 is not tiltable, rather, the support is configured to move vertically and is used to translate the x-ray source 501 to a position corresponding to the DR detector positions 504 and 506, or to intermediate positions of the DR detector 400 as just described. Thus, it should be understood that embodiments of imaging system 500 may include various combinations of one or more DR detectors 400, which may be fixed or moveable, together with an x-ray source 501 that may be tiltable and/or vertically translatable. In one embodiment, the one or more positions of DR detector 400 may overlap, resulting in a plurality of captured radiographic images that may be stitched together into one long-length digital image of the subject using known computer-implemented image reconstruction processing techniques.

FIG. 6 illustrates in schematic form another exemplary cross-section view along section 4-4 of the exemplary embodiment of the DR detector 300 (FIG. 3). Several of the components in the DR detector 600 illustrated in FIG. 6 are similar in most respects to the components as described with respect to the DR detector 400 of FIG. 4 and are identified with the same element numerals. The description of those components bearing the same element numerals is not repeated here. The DR detector 600 comprises a housing 614 having a portion made from a radiopaque material extending along a bottom portion of the DR detector 600 and also continuously forms at least one edge of the housing 614 which, in the perspective of FIG. 6, is located to the left of the interior volume 450. In separate embodiments, the radiopaque portion of the housing 614 may continuously extend long one, two, or three edges of a DR detector 600 having four edges. If the radiopaque portion of the housing 614 extends along two edges, it may extend along any two adjacent and substantially perpendicular edges or along any pair of opposite substantially parallel edges of the DR detector 600.

In the exemplary embodiment of FIG. 6, a portion of the housing 612 is formed from a radiolucent material. This portion of the housing may comprise a continuous extension of the top cover 312 (FIG. 4) to form a portion of the housing 612 for the DR detector 600 that is transparent to x-ray radiation. In separate embodiments, the radiolucent portion of the housing 612 may continuously extend along one, two, or three edges of a DR detector 600 having four edges. If the radiolucent portion of the housing 612 extends along two edges, it may extend along any two adjacent substantially perpendicular edges or along any pair of opposite substantially parallel edges of the DR detector 600. In order to fasten the radiolucent portion of the housing 612, a fastener 611, similar in material and shape as fastener 410, may be used in the bottom side of the DR detector to sealingly fasten the radiolucent edge of the housing 612 to the frame support 416 or to a frame support beam 422. At the edges of the DR detector 600 where the radiopaque housing 614 extends along the edges toward the top side 451, the fastener 410 may used as described herein to sealingly fasten it to the radiolucent portion of the housing 612. The fastener 611 is positioned in the bottom side 452 to minimize or eliminate placement of any DR detector components that are not radiolucent above, or beyond an edge of, the imaging layer 402 closest to a radiolucent edge of the DR detector 600. This helps to prevent artifacts appearing on radiographic images captured using multiple overlapping DR detectors 600 as described hereinbelow. Similarly, the integrated circuit readout electronics 424 are positioned proximate a (bottom) side of the sensor array imaging device layer 402 that is opposite the x-ray source to minimize or eliminate placement of any electronic components that are not radiolucent above, or beyond an edge of, the imaging device layer 402 closest to a radiolucent edge of the DR detector 600.

Figure 7:
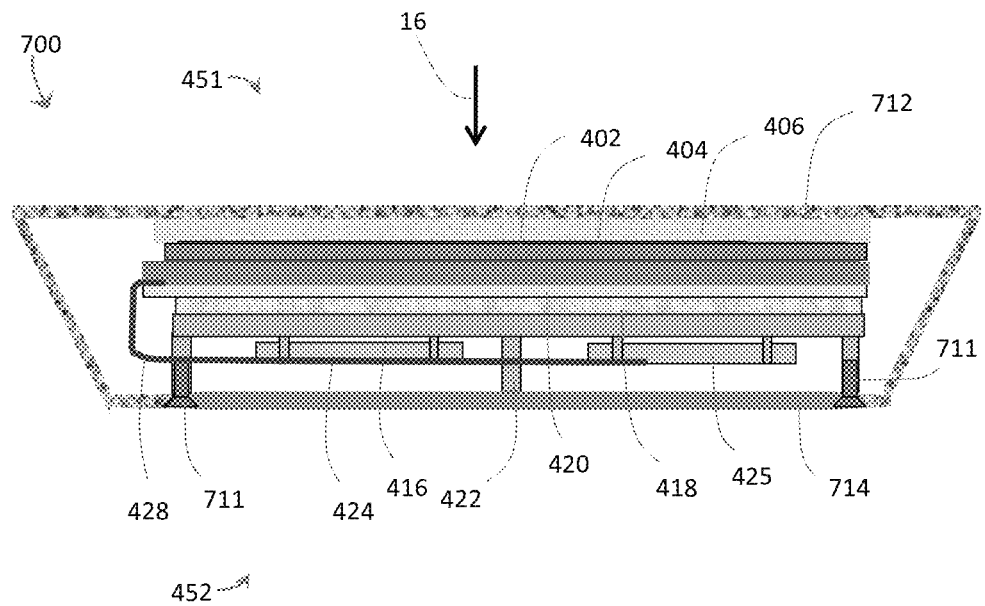
FIG. 7 is a cross-section of a portion of an exemplary portable wireless DR detector according to one embodiment.

FIG. 7 illustrates in schematic form another exemplary cross-section view along section 4-4 of the exemplary embodiment of the DR detector 300 (FIG. 3). Several of the components in the DR detector 700 illustrated in FIG. 7, such as the multilayer structure, are similar in most respects to the components as described with respect to the DR detector 400 of FIG. 4 and are identified with the same element numerals. The description of those components bearing the same element numerals is not repeated here. The DR detector 700 comprises a housing having a portion made from a radiopaque material 714 extending along a bottom portion of the DR detector 700 and may continuously form one or two edges of the housing 714 wherein, in the perspective of FIG. 7, one such edge may be located behind the multilayer structure as depicted therein. In separate embodiments, the radiopaque portion of the housing 714 may continuously extend long one or two edges of the housing 712 of the DR detector 700 having four edges. If the radiopaque portion of the housing 714 extends along two edges, it may extend along opposite edges of the DR detector 700.

In the exemplary embodiment of FIG. 7, a portion of the housing 712 is formed from a radiolucent material. This portion of the housing may comprise a continuous extension of the top cover 312 (FIG. 4) to form opposite edges of the housing 712 for the DR detector 700 that are transparent to x-ray radiation. In separate embodiments, the radiolucent portion of the housing 712 may continuously extend along two, three, or all edges of a DR detector 700 having four edges. In the perspective of FIG. 7, two opposite edges (left and right) are formed from a radiolucent material, such as a carbon fiber reinforced plastic, polymeric, or other plastic based material. The housing 712 may extend vertically between the top side and the bottom side, or it may extend at a non-orthogonal angle therebetween, as shown in FIG. 7. In order to fasten the radiolucent portion of the housing 712, fasteners 711, similar in material and shape as fastener 410, may be used in the bottom side of the DR detector to sealingly fasten the radiolucent edge of the housing 712 to the frame support 416, or to the frame support beam 422, as shown. The fasteners 711, as well as integrated circuit readout electronics 424 are positioned proximate the bottom side 452, which is a side of the sensor array imaging device layer 402 that is opposite the x-ray source to minimize or eliminate placement of any DR detector components that are not radiolucent above, or beyond an edge of, the imaging layer 402 closest to a radiolucent edge of the DR detector

600. This helps to prevent artifacts appearing on radiographic images captured using multiple overlapping DR detectors 700 as described hereinbelow.

Figure 8:
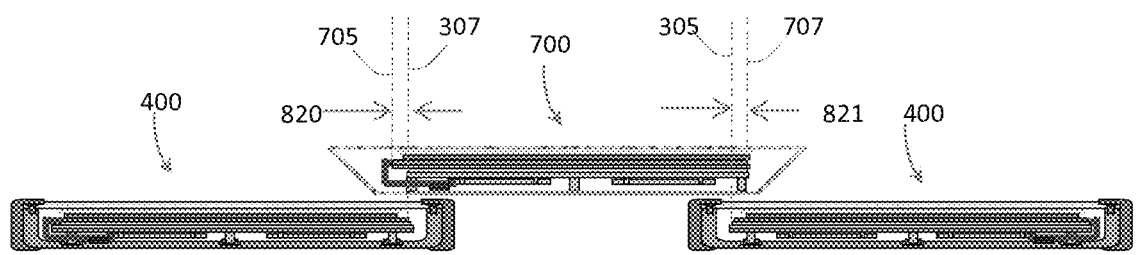
FIG. 8 is a cross-section of an exemplary arrangement of multiple DR detectors in a radiographic imaging system according to one embodiment.

As described herein, DR detector embodiments 400, 600, and 700 are usable individually, as in standard diagnostic radiographic imaging practice, and may be combined, or tiled, as described herein, for long-length imaging. FIG. 8 illustrates a side view of an exemplary arrangement of three DR detectors including two standard DR detectors 400, and a central DR detector 700, as describe herein with reference to FIG. 7, having at least two opposite edges of its housing formed from radiolucent material that each overlap one edge of one of the standard DR detectors 400, as shown. The central DR detector 700 is positioned forward of the standard DR detectors 400 in relation to an x-ray energy source positioned to emit x-rays in a direction as depicted in FIG. 4 and FIG. 7. The central DR detector includes an imaging array layer having one of its edges 705 overlapping an edge of the imaging array layer 307, in a corresponding first one of the standard DR detectors 400, by a distance 820, and an opposite edge of the imaging array layer 707 overlapping an edge of the imaging array 305, in a corresponding second one of the standard DR detectors 400, by a distance 821. The overlapping distances 820, 821 may be equivalent or different. The overlap distance is not critical to the presently disclosed invention, and may range from one or more millimeters to tens or hundreds of millimeters. Because the edges of the DR detector 700 that overlap the edges of the standard DR detectors 400 are radiolucent, and have eliminated or minimized components, such as electronic readout circuits, beyond the edges of the imaging layer 402 therein, a radiographic image captured simultaneously by the three detectors as depicted in FIG. 8, will not include unnecessary artifacts in the portions of the radiographic image captured by the standard DR detectors 400 caused by radiopaque components in the central DR detector 700 that otherwise would be disposed therein beyond the overlapping region if DR detector 700 was configured as a standard DR detector. One advantage of the embodiment depicted in FIG. 8 is that the two prior art standard detectors 400 may be used to capture a long-length image when combined as shown with only one new modified DR detector 700. The embodiment illustrated in FIG. 8 does not require obtaining several DR detectors with modified radiolucent edges. Thus, a radiographic image simultaneously captured by the three DR detectors arranged as in FIG. 8, may be accurately stitched together, without having to mask or process unnecessary artifacts, using standard computer implemented digital reconstruction techniques. Such known digital reconstruction methods include techniques for correcting geometric alignment of images from DR detectors having different source-to-image distance. In the example embodiment shown in FIG. 8, a source-to-image distance of the DR detector 700 may be less than that of the DR detectors 400.

Figure 9:
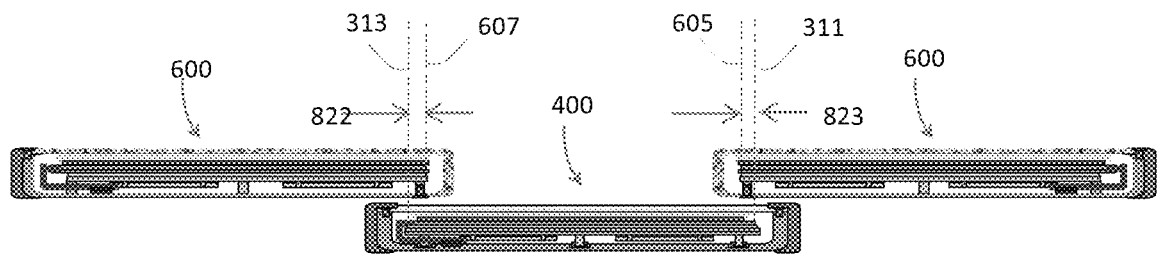
FIG. 9 is a cross-section of an exemplary arrangement of multiple DR detectors in a radiographic imaging system according to one embodiment.

FIG. 9 illustrates a side view of an exemplary arrangement of DR detectors including one standard central DR detector 400, and two DR detectors 600, as described herein with reference to FIG. 6, each having one edge of its housing formed from radiolucent material that overlaps one edge of the standard central DR detector 400, as shown. The central standard DR detector 400 is positioned rearward of the DR detectors 600 in relation to an x-ray energy source positioned to emit x-rays in a direction as depicted in FIG. 4 and FIG. 6. The central standard DR detector 400 includes an imaging array layer having one of its edges 313 overlapped by an edge of the imaging array layer 607 in a corresponding first one of the DR detectors 600 by a distance 822, and an opposite edge of the imaging array layer 311 overlapped by an edge of the imaging array layer 605 by a distance 823 in a corresponding second one of the DR detectors 600. The overlapping distances 822, 823 may be equivalent or different. The overlap distance is not critical to the presently disclosed invention, and may range from one or more millimeters to tens or hundreds of millimeters. Because the respective edge of each of the DR detectors 600 that overlaps the edge of the standard DR detector 400 is radiolucent, and has eliminated or minimized radiopaque components, such as integrated electronic read out circuits, beyond the edge of the imaging layer therein, a radiographic image captured simultaneously by the three detectors as depicted in FIG. 9, will not include unnecessary artifacts in the portion of the radiographic image as captured by the standard DR detector 400 caused by radiopaque components in the DR detectors 600 that otherwise would be disposed therein beyond the overlapping region if DR detectors 600 were configured as standard DR detectors. One advantage of the embodiment depicted in FIG. 9 is that a prior art standard detector 400 may be used to capture a long-length image when combined as shown with two new modified DR detectors 600 each having only one edge modified to be radiolucent. The embodiment illustrated in FIG. 8 does not require obtaining several DR detectors with modified radiolucent edges. Thus, a radiographic image simultaneously captured by the three DR detectors arranged as in FIG. 9, may be accurately stitched together without having to mask or process unnecessary artifacts using standard computer implemented digital reconstruction techniques. Such known digital reconstruction methods include techniques for correcting geometric alignment of images from DR detectors having different source-to-image distance. In the example embodiment shown in FIG. 9, a source-to-image distance of the DR detectors 600 may be less than that of the DR detector 400.

FIGS. 10 and 11 illustrate front or top views of the DR detector arrangements as depicted in FIGS. 8 and 9, respectively. As shown, two standard DR detectors 400 are positioned rearward of the DR detector 700 in FIG. 10, in relation to an x-ray source that, in the perspective of FIG. 10, emits x-ray energy toward the page. The DR detector 700, positioned in front, and in the middle, of the two standard DR detectors 400, includes radiolucent edges at its top and bottom edges in the Figure, which overlap the edges of the DR detectors 400, as described in relation to FIG. 8. In FIG. 11, two DR detectors 600, each as described and configured as in the description of FIG. 6, are positioned in front of the standard DR detector 400 in FIG. 11, in relation to an x-ray source that, in the perspective of FIG. 11, emits x-ray energy toward the page. The DR detectors 600 each include at least one radiolucent edge (at least the top or bottom edge) which overlaps a corresponding edge of the middle-positioned standard DR detector 400, as described in relation to FIG. 9. While particular arrangements of DR detectors have been illustrated in FIGS. 8-11, it should be noted that those skilled in the art may envisage that various combinations of DR detectors may be implemented in various geometric combinations. Thus, different types of DR detectors may be utilized in upper, middle, or lower positions, or may be used in combination with four or more detectors, having edges overlapping, wherein each of the DR detectors may be configured to include one, two, three, or four radiolucent edges. Such combinations are considered to be within the scope of the present invention so long as any radiolucent edge of a DR detector is positioned to overlap an imaging array of another DR detector. Radiopaque edges may be positioned rearward of another overlapping DR detector, or may be positioned on an exterior border of the arrangement of DR detectors. Alternatively, some or all of the tiled DR detectors may be arranged in a staggered stepwise fashion (FIG. 13), rather than having one central DR detector positioned forward or rearward of the other detectors.

FIG. 12A illustrates a DR imaging system 1200 using the arrangement of DR detectors as described in relation to FIG. 9 and FIG. 11 for use in a long-length imaging exposure. DR detector 1201 may comprise a wired or wireless DR detector of the type 600 described in relation to FIG. 6; DR detector 1202 may comprise a wired or wireless standard DR detector type of the type 400 described in relation to FIG. 4; and DR detector 1203 may comprise another wired or wireless DR detector of the type 600. X-ray source 501 may be fired once to expose a subject (not shown) to an x-ray beam 16 when the subject is placed between the x-ray radiation source 501 and the multiple DR detectors 1201-1203, to capture a distributed image of the subject that is simultaneously captured and stored by the multiple DR detectors 1201-1203. The captured images, each comprising a portion of the subject, one from each DR detector, may be stitched together using known computer implemented reconstruction techniques to generate a single long-length composite image of the subject. Part of the control operations carried out by the image processing and control unit 34 may include wired or wireless communication with the DR detectors 1201-1203 for verification that the DR detectors have been initiated and are all in a ready state before exposure, for synchronization, and for coordinating storage and identification of image frame data from each of the detectors. Such a method does not require time consuming repositioning of DR detectors 1201-1203, repositioning of the x-ray source 501, or multiple exposures, as may be currently practiced to obtain a long-length radiographic image. The arrangement of DR detectors 1201-1203 may be configured by attachment to a rigid, rollable floor stand structure 1200 using a modified "bucky" arrangement to fix in position each of the DR detectors 1201-1203, or the detectors 1201-1203 may be affixed to a wall mounted structure 1200. Alternatively, the DR detector 1202 may be part of an existing permanent radiographic imaging installation which is fixed in a relative position as shown, while the other two DR detectors 1201, 1203, may be portable DR detectors installed into the mounting structure to be temporarily used for long-length imaging. One embodiment of the present invention may comprise a retrofittable separate structure for temporarily securing in position the DR detectors 1201 and 1203 as shown and allowing movement of the structure having these two detectors 1201, 1203, to position them in front of (overlapping) the fixed installation of DR detector 1202, as will be described below in relation to FIG. 12B. Although the arrangement of DR detectors 1201-1203 has been illustrated as a vertically adjacent alignment wherein the imaging planes of the DR detectors are also vertical, it should be noted that any of the tiled arrangements of DR detectors disclosed herein may be positioned adjacent to each other in a substantially horizontal alignment wherein the imaging planes of the DR detectors are horizontal, such as may be used for a human patient who is lying down on an examination bed with an x-ray source positioned above the patient for full length body imaging, or the DR detectors disclosed herein may be placed adjacent to each other horizontally wherein the imaging planes of the DR detectors are vertical.

FIG. 12B illustrates a DR imaging system 1250 using an arrangement of DR detectors as described in relation to FIG. 12A for use in a long-length imaging exposure, except that the DR detectors 1201, 1203 are affixed to a transport apparatus 1251 comprising a support post 1254 attached to a base 1256 outfitted with means for transporting the apparatus 1251 and DR detectors 1201, 1203, such as wheels 1257 which may include freely rotatable wheels, lockable wheels, wheels that may be lowered or raised by hand cranking or by electric motor under operator control, wheels that are not motor-assisted, and motor driven wheels that may be powered by an electric motor to assist in manually transporting the apparatus 1251 by rolling it over a floor or other surface. The support post 1254 secures in a vertical relative position the DR detectors 1201, 1203, using one or more cross-beams attached to the support post 1254, with a preselected gap size therebetween 1255 sufficient for the respective bottom and top edges of the DR detectors 1201, 1203, to overlap a top and bottom edge of DR detector 1202, as previously described. As mentioned above, the DR detector 1202 may represent a standard prior art DR detector permanently installed on one wall 1252 such as in a medical facility imaging room. The DR detector 1202 may be used alone with x-ray source 501 for standard non-elongated radiographic imaging and, in the case where a long-length radiographic image may be desired, the apparatus 1251 may be rolled into position 1260 along a floor of an imaging room. Similarly, DR detectors 1201, 1203, may be portable, to be used individually for performing standard radiographic imaging of patients and may be inserted or attached to support post 1254 to configure the transport apparatus 1251 as described herein. Thus, the portable pair of DR detectors 1201, 1203, may be advantageously affixed to the transport apparatus 1251 to provide a capability to easily convert the permanent installation of the standard DR detector 1202 into the long-length imaging system 1250 when combined as shown with two new modified DR detectors of the type 600 each having one or more edges being radiolucent.

As before, x-ray source 501 may be fired once to expose a subject (not shown) when the subject is placed in front of the multiple DR detectors 1201-1203. Part of the control operations carried out by the image processing and control unit 34 may include wired or wireless communications, wherein wireless communications are represented as wireless transmission signals 1258, with the DR detectors 1201-1203, such as waiting for and synchronizing ready state signals from all activated DR detectors 1201-1203 before an exposure by x-ray source 501. Such a method does not require time consuming repositioning of one or more DR detectors 1201-1203, repositioning of the x-ray source 501, or multiple exposures, as may be currently practiced to obtain a long-length radiographic image.

FIG. 12C illustrates a front view of the transport apparatus 1251 of the DR imaging system 1250 of FIG. 12B. Stationary registration markers 1261, 1262, which may be rigidly affixed to support frame 1254, may be used to assist in properly aligning a radiographic image of a subject partially captured by each of two or more detectors 1201-1203. Precision alignment assists in digitally stitching together the captured radiographic images to form an accurate long length radiographic image of the subject. The registration markers 1261, 1262, may be made from a radiopaque material such that a portion of the registration markers 1261, 1262 appear in calibration images captured by the DR detectors 1201-1203. In one embodiment, two partial radiographic images of a subject captured simultaneously by the DR detectors 1201 and 1202 may be precisely aligned using a location of the registration marker 1261 which appears at a particular row of the photosensor array in both calibration images. In another embodiment, two partial radiographic images of a subject captured simultaneously by the DR detectors 1202 and 1203 may be precisely aligned using a location the registration marker 1262 which appears at a particular row of the photosensor array in both calibration images. In another embodiment, three partial radiographic images of a subject captured simultaneously by the DR detectors 1201-1203 may be precisely aligned using locations of the registration markers 1261, 1262, which appear at particular rows of the photosensor arrays in all three calibration images. The row location (e.g. array row number) of the marker 1261 as it appears in the calibration image captured by the detector 1201 may be aligned, for digital stitching purposes, with the row location (e.g. array row number) of the marker 1261 as it appears in the calibration image captured by the detector 1202. Similarly, the row location (e.g. array row number) of the marker 1262 as it appears in the calibration image captured by the detector 1203 may be aligned, for digital stitching purposes, with the row location (e.g. array row number) of the marker 1262 as it appears in the calibration image captured by the detector 1202, thereby allowing the three partial radiographic images of a subject captured simultaneously by detectors 1201-1203 to be precisely aligned and stitched together to form a long length image of the subject.

In an example method embodiment, the detector 1201 may be detached from its cross-beam support and the detector 1202 flashed (exposed without a subject to be imaged) by the source 501 (FIG. 12B) to capture a precise position of the marker 1261 as it appears in such a captured calibration image frame of detector 1202, such as by identifying a precise row, or rows, of the two dimensional array of photosensors where the marker 1261 appears. Thereafter, the detector 1201 may be reattached to its cross-beam support and similarly flashed by the source 501 to capture a precise position of the marker 1261 as it appears in the captured calibration image frame of detector 1201, such as by identifying a precise row, or rows (depending on photosensor resolution), of the two dimensional array of photosensors where the marker 1261 appears. Such flash exposures may also be used to capture a correction image, or correction map, of the detector's photosensor array such as a gain correction map to be used for final image correction, as described hereinbelow.

A subject to be radiographically imaged may be positioned between the detectors 1201, 1202 and the x-ray source 501, and exposed by the source 501 whereby radiographic images of the subject are captured by detectors 1201 and 1202. The radiographic exposure and image capture of the subject may take place before or after the calibration images are captured. The markers 1261-1263 may be configured to be removable or not, and may be removed prior to radiographic imaging of the subject, if desired. The captured radiographic images of the subject can then be digitally stitched together to form a long length image, using well known techniques, relying upon the precise overlap position of the marker 1261 in each corresponding photosensor row of the images as determined by the captured calibration images. The identified row in the radiographic image captured by detector 1201 may be overlapped precisely on the identified row of the radiographic image captured by the detector 1202 to determine an exact overlap alignment of the images. In a similar process, a long length radiographic image of a subject may be formed using the detectors 1202 and 1203 and marker 1262. Similarly, all three detectors 1201-1203 and the both markers 1261-1262, may be used to capture calibration images, whereby a three detector exposure and image capture of a subject may be used to form an even longer length radiographic image comprising radiographic images from all three detectors digitally stitched together. In an example method using three detectors 1201-1203, the detector 1202 may be flashed with both markers 1261 and 1262 captured in its calibration frame (while detectors 1201, 1203 are removed from the support frame 1254) to determine in which rows the markers 1261 and 1262 appear, and thereafter each detector 1201 and 1203 may be replaced onto the support frame 1254 and flashed to form their calibration images and to determine the row location of marker 1261 in the calibration image of detector 1201, and the row location of marker 1262 in the calibration image of detector 1203. The three captured radiographic images of the subject can then be digitally stitched together to form a long length image, using well known techniques, relying upon the identified overlap row locations of the markers 1261 and 1262 in each corresponding photosensor row of the overlapping images, as described above.

In another embodiment, radiopaque markers 1261, 1262, may be rigidly affixed to support frame 1254 at precisely the top and bottom row locations of the photosensor array of detector 1202. In this embodiment, calibration images may not be required to determine a row position of any of the markers 1261, 1262 in the calibration images. The markers 1261, 1262 may each be positioned such that it appears proximate an edge of a captured radiographic image of a subject. Because the markers 1261, 1262, are radiopaque they may appear in the radiographic images of the subject as white areas or points in the image. As shown in FIG. 12C, a tip of marker 1261 would appear proximate an edge of a radiographic image of a subject captured by detector 1201 and a tip of marker 1262 would appear proximate an edge of a radiographic image of a subject captured by detector 1203. Because the precise location of the markers 1261, 1262, appearing in the subject radiographic images are known to be aligned with the top and bottom rows of the photosensor array of detector 1202, a precise row overlap of the captured radiographic images of the subject as between the detector 1202 and either or both of the subject radiographic images captured by detectors 1201 and 1203 can be obtained to digitally stitch together a long length image of the subject. As detailed in the methods disclosed above, any two adjacent detectors, or all three detectors, may be used to capture a long length radiographic image of the subject.

In another embodiment, a radiopaque marker 1263 may be rigidly affixed to support frame 1254 in a similar manner as radiopaque markers 1261-1262. The markers 1261-1263 may be affixed to support frame 1254 at precisely known distances from each other. In this embodiment, calibration images may not be required to determine a row position of any of the markers 1261-1263 in the calibration images. The markers 1261-1263 may each be positioned such that it appears proximate an edge of a captured partial radiographic image of a subject. As shown in FIG. 12C, marker 1261 would appear proximate an edge of a radiographic image of a subject partially captured by detector 1201. Similarly, marker 1262 would appear proximate an edge of a partial radiographic image of a subject captured by detector 1203, and marker 1263 would appear proximate an edge of a partial radiographic image of a subject captured by detector 1202. Because the precise distance between the markers 1261-1263 are known, any of the markers 1261-1263 appearing in the partial radiographic images of the subject may be used to precisely overlap the images by a known amount and digitally stitch together the partial captured radiographic images to form a complete long length image.

Although the sizes of the markers 1261-1263 in FIG. 12C may be exaggerated, as illustrated, for clarity, their sizes may vary. In one embodiment, the marker may be a small rod, or it may be as small as a fine wire or needle. The marker may be permanently affixed to the detector or to the support structure that secures the detector in place, or it may be insertable through an opening in a side wall of the detector such as by snapping it into place or threading it through a screw hole, for example. As described in the methods above, any two adjacent detectors, or all three detectors, may be used to capture a long length radiographic image of a subject.

In one embodiment, the detectors 1201-1203 may be secured in position for radiographic imaging of a subject and flashed by the x-ray source 501 to capture an offset calibration image whereby the overlapping detector's attenuation of x-rays impacting a portion of the overlapped photosensor array is captured by the overlapped detector. Such a calibration image may be referred to as an overlap gain map, or overlap gain correction image.

Other correction images may also be captured and stored by the detectors 1201-1203 as correction maps for the photosensor array, such as gain maps or offset maps, which are then combined with captured radiographic images during image finalization to correct for deviations in individual imaging pixels of the photosensor array. As described above, the markers 1261-1263 may be also be used to align one or more correction maps captured by the detectors 1261-1263.

Figure 13A:
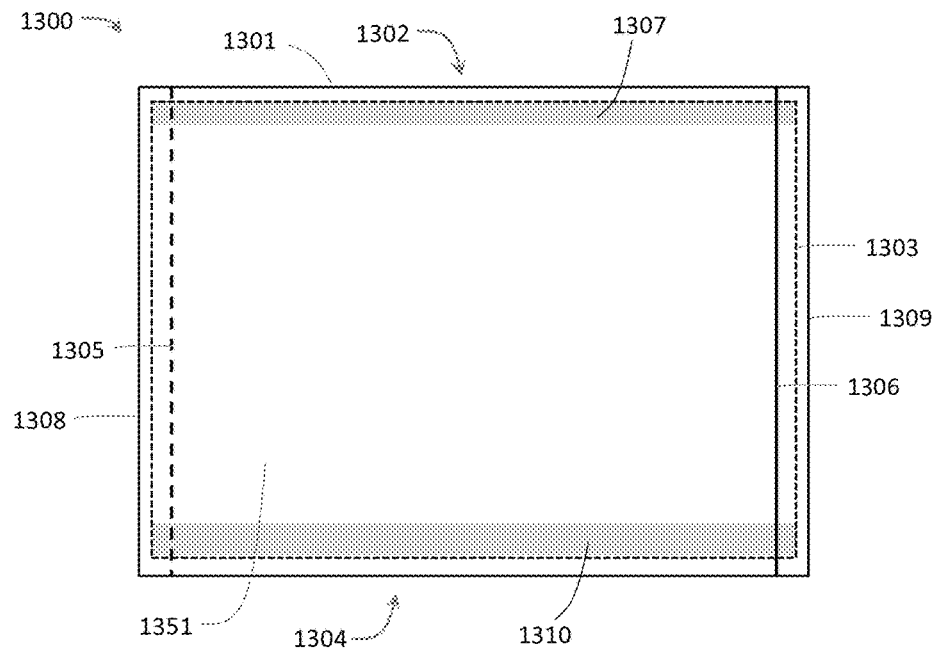
FIGS. 13A-C illustrate top, side and expanded side edge views, respectively, of the DR detector of the present invention.
Figure 13B:
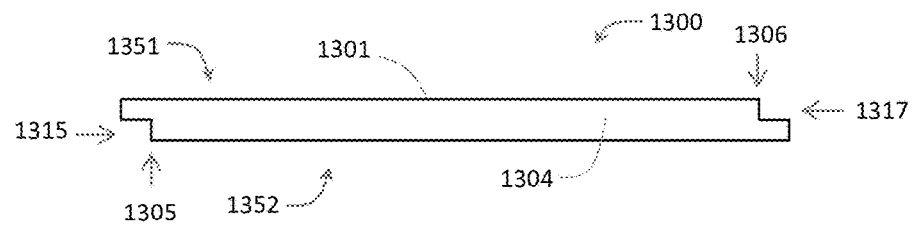
Figure 13C:
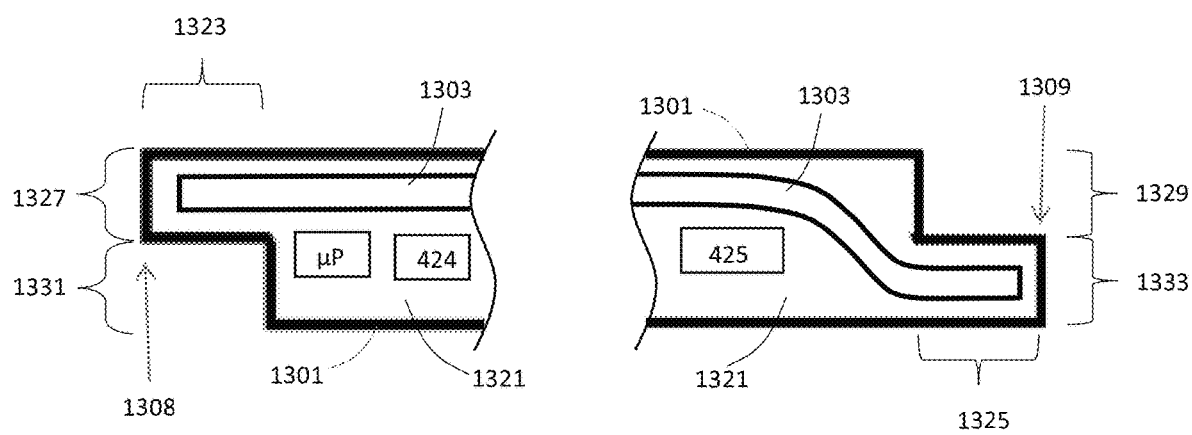

Referring to FIGS. 13A-C which shows a top, side, and expanded side edge views, respectively, of DR detector 1300, the DR detector 1300 includes at least a partially radiolucent housing 1301, which may be formed integrally such as a box having one open side and a cover for the open side, or in three or more assembled parts. The DR detector 1300 and its housing 1301 may be similar in certain respects to the DR detectors 600, 700, described herein. For orientation purposes, the DR detector 1300 may be said to include opposing sidewalls 1302, 1304, and a top surface 1351 opposite a bottom surface 1352, which top surface 1351 may be configured to face an x-ray source for DR imaging purposes. The DR detector housing 1301 includes a pair of stepped edges 1305, 1306, each at a longitudinally opposite edge of the DR detector 1300. The terminal edges 1308, 1309, of the detector 1300 extend further away from a main body portion of the detector 1300 than the stepped edges 1305, 1306, respectively. The housing 1301 encloses an imaging array layer assembly 1303 comprising at least a two dimensional DR imaging array 402 and a scintillator layer 404, as described herein. Additional layers may be included in the imaging array assembly 1303 such as a curved or flexible substrate 420, a radiopaque shield layer 418, and other support, shield, electronic, or protective layers, as desired, and as described herein. Electronic readout circuits (ROICs) 1307, 1310, may be disposed at side edges of the imaging array assembly 1303 and electrically connected to the imaging array assembly 1303. The stepped edge 1305 together with the terminal edge 1308 of the DR detector 1300 are joined by a surface of the housing 1301 to form a concave corner 1315 along one width-wise edge of the DR detector housing 1301. The concave corner 1315 may be said to face downward relative to the bottom surface 1352 of the detector 1300 which also may be said to face downward for orientation purposes. The stepped edge 1306 together with the terminal edge 1309 of the DR detector 1300 are joined by a surface of the housing 1301 to form a concave corner 1317 along another width-wise edge of the DR detector housing 1301 opposite the width-wise terminal edge 1308. The concave corner 1317 may be said to face upward relative to the top surface 1351 of the detector 1300 which also may be said to face upward for orientation purposes.

As shown in the expanded edge views of FIG. 13C, shown in cutout, the imaging array assembly 1303 extends from a position near one terminal edge 1308 of the DR detector housing 1301 to the opposite terminal edge 1309 of the DR detector housing 1301. Because the concave corners 1315, 1317, face in opposite directions (downward and upward, respectively), the imaging assembly 1303 extends in a curved formation from a position within a first housing extension 1323 proximate, and substantially parallel, to a terminal edge 1308 of the housing 1301 to a position within a second housing extension 1325 proximate, and substantially parallel, to a terminal edge 1309 of the housing 1301. The imaging assembly 1303 extends past the stepped edge 1305 in a direction away from a main body of the DR detector 1300 to a position proximate the terminal edge 1308 and past the stepped edge 1306 in a direction away from a main body of the DR detector 1300 to a position proximate the terminal edge 1309, in a curved formation. The curved formation of the imaging assembly 1303 is required, in order to extend to both terminal edges 1308 and 1309 of the detector 1300, because one housing extension 1323 is coextensive with a top surface 1351 of the DR detector housing 1301 and the other housing extension 1325 is coextensive with an opposite bottom surface 1352 of the DR detector housing 1301. A processing system 34a and other control electronics having printed circuit boards 424, 425, as described herein may be positioned within the detector housing 1301 in the space 1321 between the imaging assembly 1303 and the detector housing 1301 and electrically connected to the imaging assembly 1303.

A height (or thickness) 1327 of the housing extension 1323 is preferably configured to match a height 1329 of the stepped edge 1306, and a height (or thickness) 1333 of the housing extension 1325 is configured to match a height 1331 of the stepped edge 1305, such that a plurality of the DR detectors 1300 may be positioned adjacent to each other along their width-wise dimension (FIG. 14) so that their top surfaces 1351 are coplanar and their bottom surfaces 1352 are coplanar when an extended housing portion 1323 of one DR detector 1300 overlaps an extended housing portion 1325 of another adjacent DR detector 1300 (FIG. 14). Moreover, lengths of the housing extensions 1323 and 1325 are configured to be substantially equal so that the terminal edge 1308 of one DR detector 1300 abuts a stepped edge 1306 of an adjacent DR detector 1300 or the terminal edge 1309 of one DR detector 1300 abuts the stepped edge 1305 of an adjacent DR detector 1300 when an extended housing portion 1323 of one DR detector 1300 overlaps an extended housing portion 1325 of another adjacent DR detector 1300. Such an overlapping arrangement of a plurality of DR detectors 1300 may include two or more DR detectors 1300.

Figure 14A:
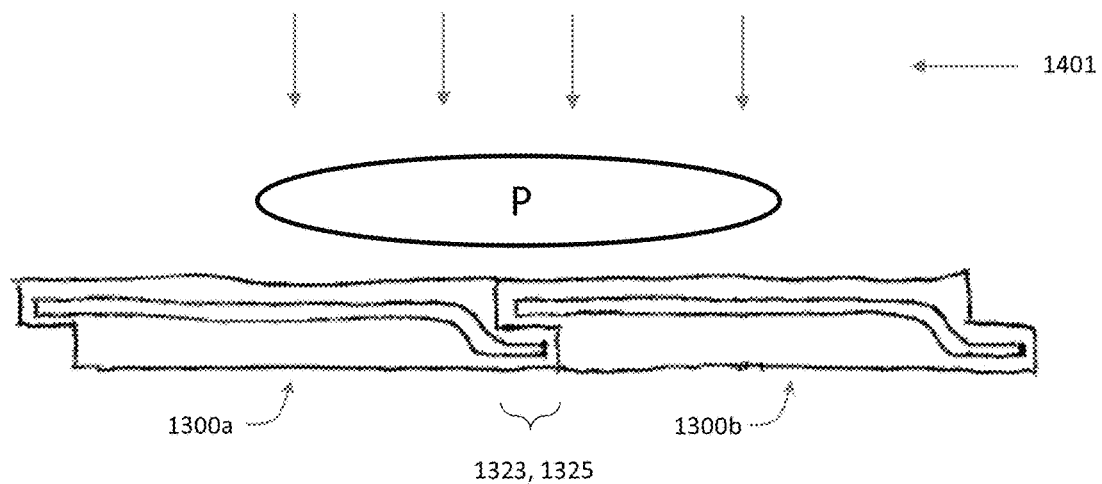
FIGS. 14A-B illustrate a side view of an x-ray system having overlapped DR detectors of the present invention and an expanded view of an overlap region of DR detectors of the present invention, respectively.

Referring to FIGS. 14A and 14 B which illustrate an overlapped configuration of a plurality of DR detectors 1300 (detectors 1300a and 1300b), a height (or thickness) 1327 of the housing extension 1323 of DR detector 1300b is preferably configured to match a height 1329 of the stepped edge 1306 of DR detector 1300a, and a height (or thickness) 1333 of the housing extension 1325 of DR detector 1300a is configured to match a height 1331 of the stepped edge 1305 of DR detector 1300b, such that a plurality of the DR detectors 1300a, 1300b, may be positioned adjacent to each other along their width-wise dimension so that their top surfaces 1351a, 1351b, are coplanar and their bottom surfaces 1352a, 1352b, are coplanar when an extended housing portion 1323 of one DR detector 1300b overlaps an extended housing portion 1325 of another adjacent DR detector 1300a. The lengths of the housing extensions 1323 and 1325 are configured to be substantially equal so that the terminal edge 1308 of one DR detector 1300b abuts a stepped edge 1306 of an adjacent DR detector 1300a and the terminal edge 1309 of the adjacent DR detector 1300a abuts the stepped edge 1305 of the one DR detector 1300b when an extended housing portion 1323 of the one DR detector 1300b overlaps an extended housing portion 1325 of the adjacent DR detector 1300a. Such an overlapping arrangement of a plurality of DR detectors 1300 may include two or more DR detectors 1300.

Figure 14B:
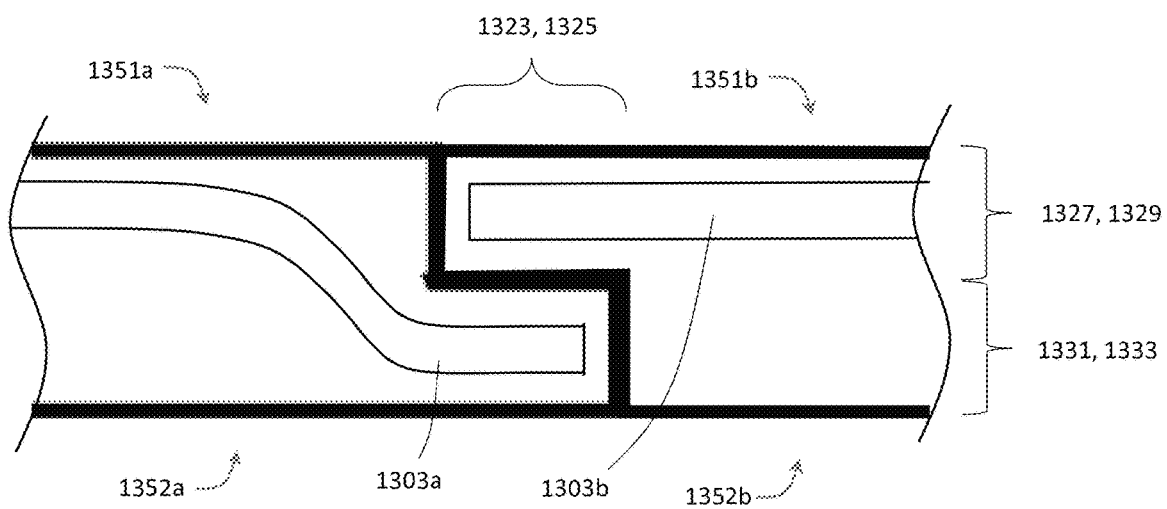

A plurality of such overlapped DR detectors 1300a, 1300b, may be positioned such that their top surfaces 1351 receive x-rays 1401 emitted by an x-ray source. A subject P may be positioned between the x-ray source and the overlapped DR detectors 1300a, 1300b, so that the overlapped DR detectors 1300a, 1300b, each capture a portion of a long length image of the subject P. As described herein, the imaging assembly 1303b in one DR detector 1300b extends past a stepped edge 1305 of the DR detector 1300b to a position proximate the terminal edge 1308 of DR detector 1300b. Similarly, as described herein, the imaging assembly 1303a in DR detector 1300a extends past a stepped edge 1306 of the DR detector 1300a to a position proximate the terminal edge 1309 of DR detector 1300a. As shown in FIG. 14B, this results in a portion of the imaging assembly 1303b within DR detector 1300b overlapping a portion of the imaging assembly 1303a within DR detector 1300a. As described herein, a DR image of the subject P, portions of which are simultaneously captured in each of the imaging assemblies 1303a, 1303b, after a single exposure of DR detectors 1300a, 1300b, respectively, may be obtained by stitching together the captured DR image portions from each of the detectors 1300a, 1300b. At least the portions of the overlapped DR detector housings of DR detectors 1300a, 1300b, shown in FIG. 14B may be made from radiolucent material as described herein. In particular, the housing extension 1323, 1325, that enclose the overlapped portions of the imaging assemblies 1303a, 1303b, may be made from radiolucent material.

As disclosed herein, a DR detector may take advantage of a thin flexible substrate to create standard size detectors (35×43 cm or 43×43 cm) such that each DR detector can overlap and attach to one another to create an imaging length of about 84 cm (two 35×43 cm detectors), or about 126 cm (three 35×43 cm detectors), or longer imaging lengths (4+ detectors). For example, a 35×43 cm detector housing can be designed so that the 43 cm sides of the imaging assembly contain space to include ROICs and the 35 cm sides do not (FIG. 13A). This enables the detectors to capture image data very close to the 35 cm edges of the detectors' housing. As shown, these detector housing edges can be stepped such that the imaging assembly of one detector overlaps another adjacent detector to create a LLI detector from two or more standard size detectors.

The overlapping detectors can be attached by mechanical means (i.e. magnet, snaps, dovetail, etc.). This enables the x-ray source and detectors to be centered on a subject anatomy to be examined. The x-ray collimation is adjusted to cover the entire imaging area and a single x-ray exposure is captured by the attached detectors. Because the imaging panels overlap, there is no patient anatomy loss. A software algorithm can discard the overlapped imaged areas so that only the region of interest remains. This method precludes the need for complex motorized and source-to-image stand synchronization (as with the tilt/translation method previously mentioned). This approach can also be used at patient bedside, much like a traditional exam with a standard DR detector, precluding the need to transport the patient to a special LLI x-ray room. X-ray dose is also expected to be less since a single one-shot exposure is taken vs. the tilting/translation method. When LLI is not required, the stepped detectors can be used as a standard 35×43 cm or 43×43 cm detector.

This description of the invention is intended to provide an overview of subject matter disclosed herein according to one or more illustrative embodiments. This description is provided to introduce an illustrative selection of embodiments. This description is intended to identify selected features of the subject matter. The subject matter is not limited to implementations that solve any or all disadvantages noted. So that the manner in which the features of the invention can be understood, a description of the invention may be had by reference to certain embodiments, some of which are illustrated in the accompanying drawings. It is to be noted, however, that the drawings illustrate certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views.

This written description uses examples to disclose the invention, including the best mode, and also to enable any person skilled in the art to practice the invention, including making and using any devices or systems and performing any incorporated methods. Such other examples are intended to be within the scope of the claims if they have structural elements that do not differ from the literal language of the claims, or if they include equivalent structural elements with insubstantial differences from the literal language of the claims.

What is claimed is:

1. A long length radiographic imaging system comprising:
a processing system;
an x-ray source communicatively coupled to the processing system;
a plurality of overlapping radiographic detectors communicatively coupled to the processing system, the plurality of overlapping radiographic detectors each comprising a housing having stepped housing edges at opposite sides of each detector, the stepped housing edges configured to each mate with a stepped housing edge of an adjacent overlapped radiographic detector, each of the plurality of overlapping radiographic detectors configured to simultaneously capture a radiographic image of a portion of a subject in a single exposure of the subject to the x-ray source.

2. The system of claim 1, wherein the plurality of overlapping radiographic detectors each comprise an imaging array enclosed within the detector housing, the stepped housing edges each comprising an extended edge portion, and wherein the imaging array in each detector extends into the extended edge portion of the stepped housing edges.

3. The system of claim 2, wherein the stepped housing edges at the opposite sides of each detector comprises a first extended edge portion coextensive with a top side of the detector and a second extended edge portion at the opposite side of the detector that is coextensive with a bottom side of the detector.

4. A digital radiographic detector comprising:
a housing;
an imaging array enclosed within the housing; and
the housing having stepped housing edges at opposite edges thereof, a first one of the stepped housing edges facing upward and a second one of the stepped housing edges facing downward, the stepped housing edges each configured to mate with a stepped housing edge of another similarly constructed digital radiographic detector.

5. The digital radiographic detector of claim 4, wherein the imaging array extends into the ends of the stepped housing edges at opposite edges thereof.

6. A long length radiographic imaging assembly comprising:
a plurality of overlapping radiographic detectors each comprising a housing having stepped housing edges at opposite sides thereof, the stepped housing edges configured to each mate with a stepped housing edge of an adjacent overlapped radiographic detector, each of the plurality of overlapping radiographic detectors configured to simultaneously capture a radiographic image of a portion of a subject in response to a single x-ray exposure.

* * * * *